United States Patent
Phan et al.

(10) Patent No.: US 9,241,664 B2
(45) Date of Patent: Jan. 26, 2016

(54) USING PHYSICAL SENSORY INPUT TO DETERMINE HUMAN RESPONSE TO MULTIMEDIA CONTENT DISPLAYED ON A MOBILE DEVICE

(75) Inventors: Thomas Phan, San Jose, CA (US); Won Jeon, Cupertino, CA (US)

(73) Assignee: Samsung Electronics Co., Ltd., Suwon-si (KR)

( * ) Notice: Subject to any disclaimer, the term of this patent is extended or adjusted under 35 U.S.C. 154(b) by 245 days.

(21) Appl. No.: 13/587,710

(22) Filed: Aug. 16, 2012

(65) Prior Publication Data
US 2014/0052682 A1 Feb. 20, 2014

(51) Int. Cl.
| | | |
|---|---|---|
| G06N 5/00 | (2006.01) |
| G06F 1/00 | (2006.01) |
| A61B 5/16 | (2006.01) |
| A61B 5/00 | (2006.01) |
| A61B 5/01 | (2006.01) |
| A61B 5/021 | (2006.01) |
| A61B 5/024 | (2006.01) |
| A61B 5/08 | (2006.01) |

(52) U.S. Cl.
CPC ............. *A61B 5/165* (2013.01); *A61B 5/0022* (2013.01); *A61B 5/167* (2013.01); *A61B 5/01* (2013.01); *A61B 5/021* (2013.01); *A61B 5/024* (2013.01); *A61B 5/0816* (2013.01); *A61B 5/6898* (2013.01)

(58) Field of Classification Search
CPC ........... G06N 5/02; G06N 5/022; G06N 5/04; G06Q 10/00
USPC .......................................... 600/409; 704/246
See application file for complete search history.

(56) References Cited

U.S. PATENT DOCUMENTS

| | | | |
|---|---|---|---|
| 2008/0214903 A1* | 9/2008 | Orbach ........................ 600/301 |
| 2009/0077160 A1 | 3/2009 | Svendsen et al. |
| 2009/0197236 A1 | 8/2009 | Phillips, II |
| 2011/0066498 A1 | 3/2011 | Wojcicki et al. |
| 2011/0099209 A1 | 4/2011 | Noh |
| 2011/0212717 A1* | 9/2011 | Rhoads et al. ............... 455/420 |
| 2011/0238379 A1* | 9/2011 | Misra et al. .................. 702/187 |

FOREIGN PATENT DOCUMENTS

| | | |
|---|---|---|
| JP | 2004-350033 | 9/2004 |
| JP | 2010-253141 | 11/2010 |

OTHER PUBLICATIONS

Verkasalo, "*Analysis of Smartphone User Behavior*," 2010 Ninth International Conference on Mobile Business / 2010 Ninth Global Mobility Roundtable, Athens, Greece, Jun. 13-Jun. 15, 2010.

(Continued)

*Primary Examiner* — Jeffrey A Gaffin
*Assistant Examiner* — Kalpana Bharadwaj
(74) *Attorney, Agent, or Firm* — Sherman IP LLP; Kenneth L. Sherman; Steven Laut

(57) ABSTRACT

A mobile handset device collects sensor data about the physiological state of the user of the handset. The mobile handset device receives multimedia content, which is consumed on the mobile handset. In a deployment phase, the sensor data is used to classify the user's emotional response to individual pieces of media content consumed on the mobile device. A classification model built in a training phase may be used to map sensor data to classification labels indicative of the user's emotional response to multimedia.

22 Claims, 3 Drawing Sheets

(56) References Cited

OTHER PUBLICATIONS

N. Lee, A. Broderick, and L. Chamberlin. "*What is neuromarketing? A discussion and agenda for future research*," International Journal of Psychophysiology, issue 63, pp. 199-204, 2007.

N. Gacioppo and R. Petty. "*Physiological responses and advertising effects: Is the cup half full or half empty?*", Journal of Psychology and Marketing, vol. 2, No. 2, pp. 115-126, Summer 1985.

Y. Chung. "*Processing Web Ads: The Effects of Animation and Arousing Content*", Cambria Press, Amherst, New York, pp. 1-11, 2007.

European Search Report dated Feb. 24, 2015 for European Application No. 13165380.0 from European Patent Office, pp. 1-8, Munich, Germany.

\* cited by examiner

US 9,241,664 B2

USING PHYSICAL SENSORY INPUT TO DETERMINE HUMAN RESPONSE TO MULTIMEDIA CONTENT DISPLAYED ON A MOBILE DEVICE

FIELD OF THE INVENTION

The present invention is generally related to evaluating the effectiveness of multimedia content provided to a mobile handset device, such as documents, videos, music, and applications received and consumed on a mobile handset device. More particularly, the present invention is directed to determining a likely emotional state of a user in response to multimedia content consumed on a mobile handset device.

BACKGROUND OF THE INVENTION

Users of a mobile handset device (or "smartphone"), have the opportunity to view a variety of different documents, photos, videos, music, applications, and other types of multimedia on their smartphone. For the creators and publishers of the multimedia content (such as designers, authors, artists, and programmers), getting feedback on the content from users is very important, as it drives the content creators and publishers to improve their products and to direct their efforts to new opportunities.

However, getting feedback from users on the quality of multimedia content used on a mobile handset is difficult. Current state-of-the art approaches include, but are not limited to: having users review the content through a quantitative metric system, such as through a rating scale of one to five stars or through written text, either of which can be given at an online or physical store; and measuring the indirect lift of the media by measuring sales of associated products, or visits to the store or website of the creator or publisher. All of these conventional approaches are problematic because the user must actively provide an evaluation of the multimedia, where such an evaluation is susceptible to bias or memory recall.

Another approach is counting the number of times that the user consumes the multimedia (by reading, watching, or listening). However, this count can still be inaccurate and too coarse. For example, many multimedia files are consumed only once (such as media received via email), so a conclusion from access counts is inadequate.

SUMMARY OF THE INVENTION

An apparatus, system, method, and computer program product is described as one that provides feedback on the emotional reaction of a user to multimedia consumed on a mobile handset device. The feedback is based on sensor data of the physiological state of a user collected by a mobile device (e.g., a smartphone) when the user views multimedia. The sensor data may be based on sensors within the mobile handset, as well as sensors in close proximity to the handset. The sensor data is indicative of a physiological response of the user to multimedia such that the sensor data also has an association with the emotional reaction of the user to the multimedia. In one embodiment, the system is divided into training and deployment phases. In the training phase, subjects provide a self-assessment of their emotional reaction to test multimedia, and this information is combined with sensor data to create a classification model having pre-selected classification labels. In the deployment phase, a mobile device may use the classification model to generate a classification label corresponding to the emotional reaction of the user of the mobile device. The classification label is then sent as feedback to another entity, such as a middleware vendor. Information from multiple mobile handset users may be aggregated to generate information for publishers and creators of multimedia content.

DETAILED DESCRIPTION

Figure 1:
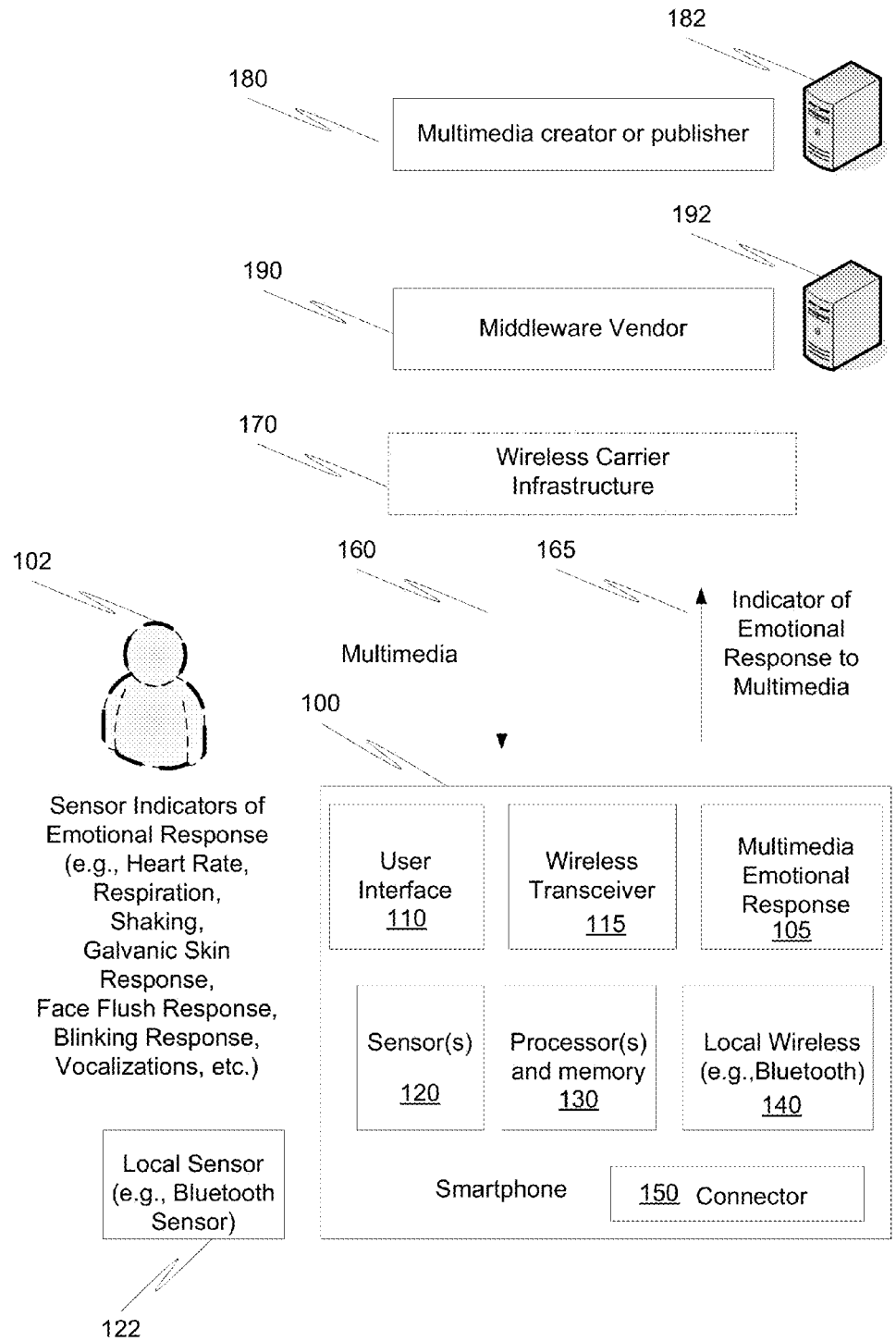
FIG. 1 illustrates an exemplary system to collect multimedia feedback through mobile handset sensory input in accordance with one embodiment of the present invention.

FIG. 1 is a high-level block diagram of a system to record, interpret, and collect users' responses to multimedia content rendered on a mobile communications device, such as smartphone, in accordance with one embodiment of the present invention. A mobile handset device 100 includes a wireless transceiver 115 and a processor and memory 130. The mobile handset device 100 is capable of wirelessly accessing the Internet, where such a handset is also commonly known as a smartphone. The mobile handset device 100 receives content from a multimedia creator or publisher 180 (e.g., Google®). A publisher 180 may, for example, utilize a server system 182 having one or more processors and memory to serve content that consumers download on their mobile handsets. A middleware vendor 190 may also use a server system 192 having one or more processors and a memory. The middleware vendor 190 can be any party that provides software that serves as an intermediary between the multimedia creator or publisher 180, providing media content to the mobile handset device 100. For example, a company providing the software Operating System (OS) of the mobile handset device 100 could also serve as a middleware vendor 190. One of ordinary skill in the art would also understand that content is made available to a mobile handset device 100 using the infrastructure of a wireless carrier 170.

The mobile handset device 100 includes a user interface 110 having a display capable of displaying multimedia along with an audio output. A multimedia emotional response module 105 collects locally available sensor data from sensor(s) proximate to the mobile handset device 100, including sensors 120 within the mobile handset device 100, and any sensors 122 coupled to the mobile handset device 100, via a local wired connection interface 150 or wireless connection interface 140.

The sensor data corresponds to the physiological response of the user 102 to multimedia 160 received and consumed on the mobile handset device 100. The mobile handset device 100 generates an indicator 165 of the emotional response to the consumed multimedia based on the sensor data. For example, if a user consumes a video clip by viewing it on the user interface 110 of the mobile handset device 100, then the sensors 120 and 122 may capture physiological changes, such as changes in heart rate, from which an indication of the user's emotional response to the multimedia may be inferred.

The multimedia emotional response module 105 may be implemented in software or firmware, and includes computer code residing on a memory. The multimedia emotional response module 105 generates feedback 165 that is indicative of the emotional response to multimedia. As examples, the feedback 165 may include a summary of relevant sensor data, or an interpretation of the sensor data based on a model. It will also be understood that feedback 165 may include a marker, timestamp, or other means to associate the feedback with a particular pieces of multimedia content.

The multimedia includes media such as documents, pictures, videos, music, and non-musical audio, such as an audio narration (e.g., an audio book). Additionally, multimedia can include multimedia applications received and consumed at the mobile handset device 100. Multimedia, as used in this application, does not include advertisements.

In one embodiment, the multimedia emotional response module 105 determines a category of emotional response of the user, based on a model of the user's emotional state, with respect to different haptic and biometric sensor measurements from the data available from sensor(s) 120 and 122. Examples of sensor data include the user's heart rate, respiration, shaking, galvanic skin response, face flush response, blinking response, and vocalization. The categories of emotional response may be categories relevant to advertisers based on a classification model, such as whether the emotional state of the user indicates a favorable or unfavorable emotional response to a piece of multimedia. The users' emotional responses to multimedia are identified and collected, providing a source of information for the publisher 180, to gauge the effectiveness of multimedia 160. Additionally, if the multimedia is sufficiently long, feedback on the user's response to different segments of the multimedia may be obtained.

Examples of sensor(s) 120 available in a mobile handset device capable of serving as physiological sensors of the user 102 of the mobile handset device 100 include a high-resolution front-facing color video camera, a microphone, a Global Positioning System (GPS) or other location sensor, and an accelerometer to sense motion (acceleration, shaking, and movement). Front-facing camera data may be analyzed to determine a blushing response, eye tracking (gaze location and duration, as well as blinking behavior), facial expression, or other visual indicators of the emotional state of the user. There is a trade-off between sensor quality and the ability to detect meaningful physiological responses in a wide range of user environments and noise conditions. For gaze detection, exemplary minimum camera requirements are 4 Megapixels and 20 frames per second. An exemplary accelerometer implementation has an accuracy of at least 95% of true acceleration in units of meters per second squared. Analysis of motion sensor data may provide information on whether the user is shaking and/or makes abrupt movements indicative of a strong emotional response. Audio data may be analyzed to provide indicators of emotional response, such as audible gasps.

Other examples of sensor(s) 120 may include other types of compact sensors capable of being integrated into the mobile handset device 100 to increase security and to support health and fitness applications, such as heart rate monitors, temperature sensors, pressure sensors, and humidity (skin dampness) sensors.

Additionally, a local sensor 122 may be in communication with the mobile handset device 100 via a wired connector 150. However, more generally local sensor 122 may have a local wireless connection with the mobile handset device 100. For example, a user may have portable and/or wearable body sensors that are in communication with the mobile handset device 100 via a wireless connection, such as Bluetooth®. Those of ordinary skill in the art will recognize that other wireless communication standards can be used in the place of Bluetooth®, such as the Zigbee® and Ant+™ wireless standards. In a preferred implementation, Bluetooth® is used. The Bluetooth® 4.0 standard supports wearable health sensors, such as a heart-rate profile and a thermometer profile. Other examples of wireless sensors using Bluetooth® communication include Bluetooth® enabled sensors to measure heart-rate, temperature, and galvanic skin response.

The sensor data is captured directly on the mobile handset device 100 by the multimedia emotional response module 105. However, the analysis of haptic and biometric sensory inputs can be performed either on the mobile handset device 100 or a summary of the data can be sent back to the publisher or advertiser for analysis.

User privacy can be guarded by various means. For example, aspects of the user's identity could be partially or completely cloaked from publishers or advertisers to preserve privacy using a privacy protection protocol. Moreover, information aggregation techniques may be used to aggregate responses from multiple users to generate aggregated data, preserving the privacy of individual user identity information. Additionally, in a preferred implementation, the user is given the option to either opt-in or opt-out of the use of the system.

The system of the present invention thus supports methods to record, interpret, and collect users' responses to delivered media. A particular user's response is captured through haptic and biometric sensory inputs of the mobile handset device 100, such as the shaking of the handset captured via readings of the accelerometer, or a change in the user's heartbeat captured via a Bluetooth®-connected heart-rate monitor. Once the data is collected, it can be analyzed by first filtering out noise from the readings, and then, deriving a conclusion on how the user responded to the multimedia. A conclusion can then be aggregated across all users, with the results being used by the publisher.

In one embodiment of the invention, sensory input information is analyzed at the mobile handset device 100 to return an abstracted representation of the user's response, such as a representation for enjoyment, dislike, or apathy. This analysis can be performed through various methods, including but not limited to: rule-based analysis by deriving abstract responses through threshold levels of sensory input; or classification through supervised machine learning methodologies such as decision trees, Hidden Markov Models, or Support Vector Machines.

A particular user's response is captured through haptic and biometric sensory inputs of the mobile handset device 100, such as the shaking of the handset captured via readings of the accelerometer, a change in the user's heartbeat captured via a Bluetooth®-connected heart-rate monitor, a change in the user's facial features measured by a front-facing camera, or a change in the skin conductance of the user measured by a galvanic skin response sensor. Once the data is collected, it can be analyzed by first filtering out noise from the readings, and then, deriving a conclusion on how the user responded to the multimedia. This analysis can be performed either on the device or at a middleware vendor 190's server. A conclusion can then be aggregated across all users, with the results being used by the publisher or creator of the multimedia.

The advantage of this approach is that the users' response can be measured automatically without the need for the users to explicitly provide purposed feedback to the publisher or creator. Additionally, the information captured by the invention is potentially more accurate than user responses since it is difficult for people to consciously control their physiological manifestations. Furthermore, since the automated approach of the invention measures these physiological responses directly, the effect of bias or memory lapse from the user is minimized.

Figure 2:
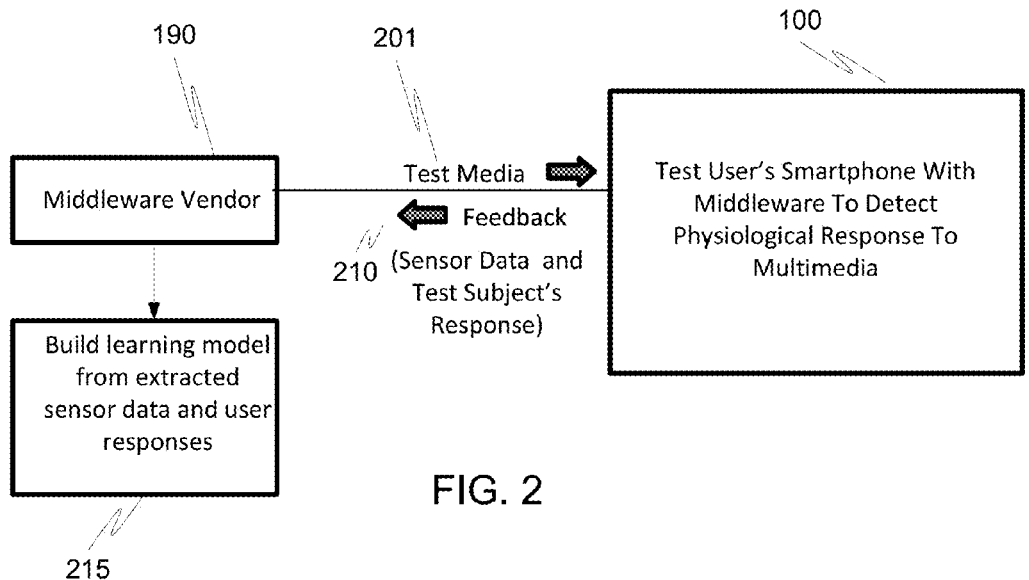
FIG. 2 illustrates a training phase to form associations between classification labels and sensory data in accordance with one embodiment of the present invention.

FIG. 2 shows initial steps carried out by an entity in a training phase to collect training data from test participants, and to create a statistical model to map sensory input data to a labeled response. An association model may be used to map sensory data to a high-level interpretation of emotional response, including a set of classification labels such as strongly like, like, neutral (apathetic), dislike, and strongly dislike. It would be understood that the exact number and type of classification labels may be varied.

Prior to training, the middleware vendor 190 creates, in step 201, sensor-recording software on the mobile handset device 100 to record sensor input, and to allow training participants to view multimedia. The recorded sensor input can include, but is not limited to, an accelerometer, a galvanic skin response sensor, a microphone, and a heart-rate monitor.

Training begins when the training participant activates the smartphone's software to view test multimedia 210 that is shown to them. Additionally, the training participants record their labeled response to the content. At the same time, the sensors record their physical response. This feedback 210 is provided to the middleware vendor 190. That is, each test participant views media, their physiological reaction is recorded via the sensors, and each test participant also notes their emotional reaction (i.e., the participant is polled about what they perceive their emotional reaction to the test multimedia is). Long-duration multimedia can use aggregate statistics (such as mean, median, or standard deviation) for the entire multimedia (or for segments thereof, such as scenes in a movie). Additionally, instantaneous measurements at particular points in time may be collected.

The middleware vendor 190 retrieves the labeled training data from all training participants and extracts features to build a learning model 215. The extracted features can include, but are not limited to, skin conductance (as measured in units of ohms by a galvanic skin response sensor), heart-rate (as measured in units of beats per minute by a heart-rate monitor), facial response (as measured in units of blush color or eyeblinks per second by a front-facing video camera on the phone), and shaking of the handset (as measured in units of gravitational acceleration as measured by an accelerometer). Additional features can include, but are not limited to: ribcage expansion to measure breathing, and eye tracking. Moreover, in addition to average information, it will be understood that the time-rate characteristics of the responses may also be analyzed. These features, and the label activity, are then given as input into a machine learning algorithm, such as for a decision tree, support vector machine, maximum entropy, or k-nearest-neighbor.

Figure 3:
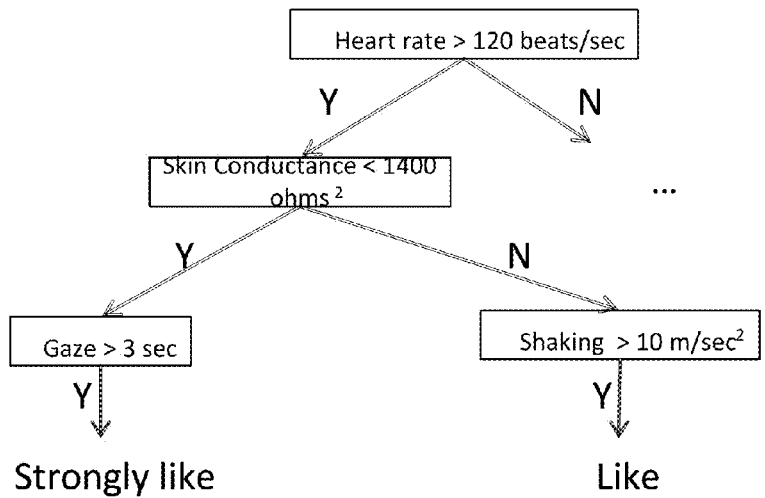
FIG. 3 illustrates an exemplary decision tree that maps ranges of sensory data to two exemplary classification labels in accordance with one embodiment of the present invention.

A statistical model 215 is then built that maps the sensor data to the responses of test participants. In a preferred embodiment, the well-known ID3 algorithm is to create a decision tree that will perform this mapping. The decision tree will take the form of a binary tree with one root connected by edges to interior vertices, which in turn, are connected by edges to other vertices. The leaf vertices in this tree are the classification labels. The root and interior vertices contain decision statements that must be evaluated, with the result of the decision at that vertex determining which outgoing edge to take. The role of the ID3 algorithm is to create a tree that is reasonably sized and provides accurate mappings from features to classification labels. Note that the ID3 algorithm will produce different decision trees based on different data. An example portion of a produced decision tree based on some input data is illustrated in FIG. 3.

Figure 4:
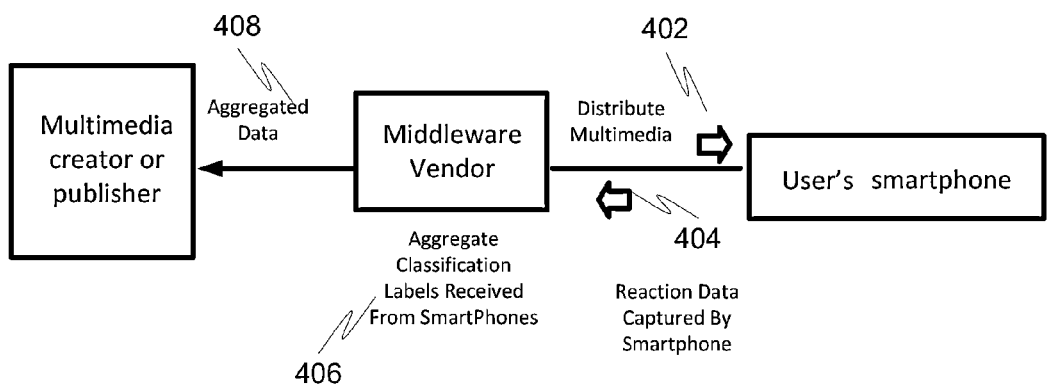
FIG. 4 illustrates a deployment phase to generate real-time feedback for multimedia content in accordance with one embodiment of the present invention.

In a deployment phase, the decision tree (or other learning model) is deployed to individual smartphones. The middleware vendor 190 writes and deploys classification software that accepts the statistical model (developed during the training phase), and the user's current sensor data. The software is activated and runs in the background of a smartphone. The software classifies the user's sensor data using the model, and produces a perceived response FIG. 4 shows how the decision tree is used in a deployment phase to perform classification of the emotional response of a user to multimedia consumed on the mobile handheld device 100.

In step 402, multimedia media is distributed to an individual user via their smartphone. Upon exposure to multimedia, the user may react to the multimedia. The user's response is captured through haptic or biometric sensory input, and features are extracted. For example, the user may respond by shaking the smartphone (which can be measured through an accelerometer) or by increasing his or her heart-rate (which can be measured through a Bluetooth®-connected heart-rate monitor). In one embodiment of the invention, this sensory input information is analyzed at the smartphone to return an abstracted representation of the user's response, such as a representation for enjoyment, dislike, or apathy.

In step 404, the user's response is sent back to the middleware vendor 190. Additionally, the response of other users is also sent back to the middleware vendor 190. For example, if a thousand copies of a music file are sent to a thousand different smartphones, then each user's response may be determined on their respective smartphone and sent back to the middleware vendor 190.

In step 406, the middleware vendor 190 collects and aggregates the users' responses for the multimedia from different smartphones. Aggregate information may include the average user response, the percentage of users who enjoyed the multimedia, and the percentage of users who disliked the multimedia.

In step 408, the middleware vendor 190 sends aggregated information back to the multimedia creator or publisher 180.

Modifications and alternations are also contemplated. In one embodiment, the sensory input is collected at each smartphone, but is not analyzed. Instead, summary statistics may be measured, such as average accelerometer readings or average heartrate. These summary statistics are sent back the middleware vendor 190. The middleware vendor 190 then collects and aggregates the user's response to multimedia and performs and analyzes the emotional response of each user.

While the invention has been described in conjunction with specific embodiments, it will be understood that it is not intended to limit the invention to the described embodiments. On the contrary, it is intended to cover alternatives, modifications, and equivalents as may be included within the spirit and scope of the invention, as defined by the appended claims. The present invention may be practiced without some or all of these specific details. In addition, well known features may not have been described in detail to avoid unnecessarily obscuring the invention.

In accordance with the present invention, the components, process steps, and/or data structures may be implemented using various types of operating systems, programming languages, computing platforms, computer programs, and/or general purpose machines. In addition, those of ordinary skill in the art will recognize that devices of a less general purpose nature, such as hardwired devices, field programmable gate arrays (FPGAs), application specific integrated circuits (ASICs), or the like, may also be used without departing from the scope and spirit of the inventive concepts disclosed herein.

The present invention may also be tangibly embodied as a set of computer instructions stored on a computer readable medium, such as a memory device.

What is claimed is:

1. A mobile handset device, comprising:
    at least one processor and a memory;
    a user interface having a display;
    a multimedia response processor within the mobile handset device configured to collect sensor data from a set of sensors internal to the mobile handset device, the set of sensors comprising one or more cameras, and a motion sensor, the sensor data indicative of a physiological response of a user holding the mobile handset device; and
    the multimedia response processor monitoring sensor data associated with the physiological response of the user to multimedia consumed on the mobile handset device and generating an output indicative of the emotional response of the user to the multimedia based on the sensor data associated with the physiological response generated by holding the mobile handset device.

2. The mobile handset device of claim 1, wherein the mobile handset device includes a haptic sensor on the mobile handset device that provides sensor data based on touching the mobile handset device.

3. The mobile handset device of claim 1, wherein the multimedia response processor is configured to determine a classification label of user emotional state by associating sensor data with a classification model and reporting on classification determination.

4. The mobile handset device of claim 3, wherein the reporting is utilized to generate aggregate data for a plurality of emotional responses determined by multiple mobile handset devices for a media creator or publisher.

5. The mobile handset device of claim 1, wherein the multimedia response module includes a training phase to determine an association between sensor data and user emotional state.

6. The mobile handset device of claim 5, wherein in the training phase, a user is polled on her emotional response to test multimedia to provide user polling data, and to determine an association between sensor data and classification labels for emotional response.

7. The mobile handset device of claim 1, wherein the sensor data includes sensor data indicative, directly or indirectly, of a heart rate, respiration rate, galvanic skin response, temperature, pressure, acceleration, motion response, skin flush response, eye blinking response, and a vocal response.

8. A method of analyzing the effectiveness of multimedia displayed on a mobile handset device, comprising:
    providing multimedia to a multiplicity of mobile handset devices, where each mobile handset device is configured to record sensor data from internal sensors comprising one or more cameras and a motion sensor, wherein the sensor data is indicative of a physiological response of a user holding the mobile handset device;
    receiving indicator data from each of the multiplicity of mobile handset devices, the indicator data being indicative of the emotional response to a particular piece of multimedia played by the respective mobile handset device; and
    determining an aggregated emotional response classification label for at least one piece of multimedia.

9. The method of claim 8, wherein the indicator data includes an emotional classification label within a classification model based on a summary of sensor data.

10. The method of claim 8, further comprising in a training phase requesting test subjects to provide a self-assessment of emotional state in response to test multimedia.

11. The method of claim 8, further comprising generating a classification model mapping a set of classification labels to sensor data.

12. The method of claim 8, further comprising providing aggregated emotional response information to each provider of the at least one piece of multimedia.

13. A method of analyzing the effectiveness of multimedia, comprising:
    receiving indicator data from internal sensors of a multiplicity of mobile handset devices that is indicative of the emotional response to multimedia consumed by users based on holding of individual mobile handset devices, the internal sensors comprising one or more cameras and a motion sensor; and
    aggregating the indicator data and determining an average emotional response within a classification model for at least one piece of multimedia content.

14. The method of claim 13, wherein the indicator data includes a summary of sensor data provided by individual mobile handset devices.

15. The method of claim 14, wherein the indicator data includes a classification label generated by individual mobile handset devices according to a classification model.

16. The method of claim 13, further comprising providing a classification model mapping a set of emotional response classification labels to a tree of physiological sensor data ranges for a user of the mobile handset device.

17. A non-transitory processor-readable medium that includes a processor executable program, to perform a method comprising:
    collecting sensor data from a set of sensors proximate to a mobile handset device indicative of a physiological response of a user of the mobile handset device to multimedia consumed on the mobile handset device, wherein the set of sensors comprise internal sensors of the mobile handset device including one or more cameras and a motion sensor; and
    generating an output indicative of an emotional response of the user to at least one piece of multimedia based on the sensor data generated by holding the mobile handset device.

18. The non-transitory processor-readable medium of claim 17, wherein the processor executable program to perform the method further comprising associating sensor data with a classification model and determine a classification label for the emotional response of the user to a piece of multimedia.

19. The non-transitory processor-readable medium of claim 17, wherein the processor executable program to perform the method further comprising determining an association between sensor data and an emotional response of the user to multimedia.

20. The non-transitory processor-readable medium of claim 17, wherein the processor executable program to perform the method further comprising providing user polling data to determine an association between sensor data and emotional response to media in a training phase.

21. The mobile handset device of claim 1, wherein the set of sensors comprises a front camera and a rear camera on the mobile handset device for capturing visual sensor data indicative of a physiological response of a user holding the mobile handset device.

22. The mobile handset device of claim 1, wherein the set of sensors comprises a microphone for capturing audio sensor data indicative of a physiological response of a user of the mobile handset device.

\* \* \* \* \*